US006892884B1

(12) United States Patent
Fernandez

(10) Patent No.: US 6,892,884 B1
(45) Date of Patent: May 17, 2005

(54) INFANT ACCESSORY SYSTEM AND METHOD OF MAKING THE SAME

(76) Inventor: Michelle L. Fernandez, 607 Mission Hills Dr., Arlington, TX (US) 76018

( * ) Notice: Subject to any disclaimer, the term of this patent is extended or adjusted under 35 U.S.C. 154(b) by 30 days.

(21) Appl. No.: 10/622,941

(22) Filed: Jul. 18, 2003

(51) Int. Cl.[7] .............................................. B65D 73/00
(52) U.S. Cl. ...................... 206/494; 206/216; 206/457; 206/497; 604/390
(58) Field of Search ................................ 206/216, 223, 206/494, 497, 499, 457, 581, 812; 604/385.13, 604/385.3, 386, 389, 390, 391, 396

(56) References Cited

U.S. PATENT DOCUMENTS

| | | | | |
|---|---|---|---|---|
| 3,620,217 A | * | 11/1971 | Gellert | ........................ 604/390 |
| 3,869,761 A | * | 3/1975 | Schaar | ........................ 604/390 |
| 4,461,790 A | * | 7/1984 | Snider | ........................ 206/457 |
| 4,743,240 A | | 5/1988 | Powell | |
| 5,071,414 A | * | 12/1991 | Elliott | ................... 604/385.13 |
| 5,718,100 A | * | 2/1998 | Petty | ........................ 206/457 |
| 5,855,276 A | | 1/1999 | Smith, Jr. | |
| 5,947,277 A | * | 9/1999 | Sherman | ..................... 206/216 |
| 5,957,325 A | | 9/1999 | Montanez | |

* cited by examiner

Primary Examiner—Luan K. Bui
(74) Attorney, Agent, or Firm—Leonard & Proehl; Mark Ekse

(57) ABSTRACT

An infant accessory system and method of making the same for providing an array of necessary infant care items. The infant accessory system and method of making the same includes a base layer, an intermediate layer, and a top layer. The base layer includes a plurality of diapers rolled to form a cylindrical base. The base layer includes a first diameter. The intermediate layer includes a second diameter less than the first diameter. The intermediate layer includes a second plurality of diapers rolled to form a cylindrical intermediate stage. The intermediate layer is positioned on top of the base layer. The top layer includes a third diameter less than the second diameter. The top layer includes a third plurality of diapers rolled to form a cylindrical top layer. The top layer is positioned on top of the intermediate layer.

15 Claims, 2 Drawing Sheets

INFANT ACCESSORY SYSTEM AND METHOD OF MAKING THE SAME

BACKGROUND OF THE INVENTION

1. Field of the Invention

The present invention relates to baby accessory holders and more particularly pertains to a new infant accessory system and method of making the same for providing a collection of necessary supplied.

2. Description of the Prior Art

The use of accessory holders is known in the prior art. U.S. Pat. No. 5,957,325 describes a disposable diaper storage system. Another type of baby accessory holders is U.S. Pat. No. 4,743,240 having a container for holding both new and used disposable diapers.

While these devices fulfill their respective, particular objectives and requirements, the need remains for a system that provides a variety of necessary items which may be used for emergency purposes or in the regular course of caring for an infant.

SUMMARY OF THE INVENTION

The present invention meets the needs presented above by providing a wide array of accessories, each independently accessible.

Another object of the present invention is to provide a new infant accessory system and method of making the same that can be made as part of a baby shower.

Still another object of the present invention is to provide a new infant accessory system and method of making the same that can be used with new accessories as well as family mementos.

To this end, the present invention generally comprises a base layer, an intermediate layer, and a top layer. The base layer includes a plurality of diapers rolled to form a cylindrical base. The base layer includes a first diameter. The intermediate layer includes a second diameter less than the first diameter. The intermediate layer includes a second plurality of diapers rolled to form a cylindrical intermediate stage. The intermediate layer is positioned on top of the base layer. The top layer includes a third diameter less than the second diameter. The top layer includes a third plurality of diapers rolled to form a cylindrical top layer. The top layer is positioned on top of the intermediate layer.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
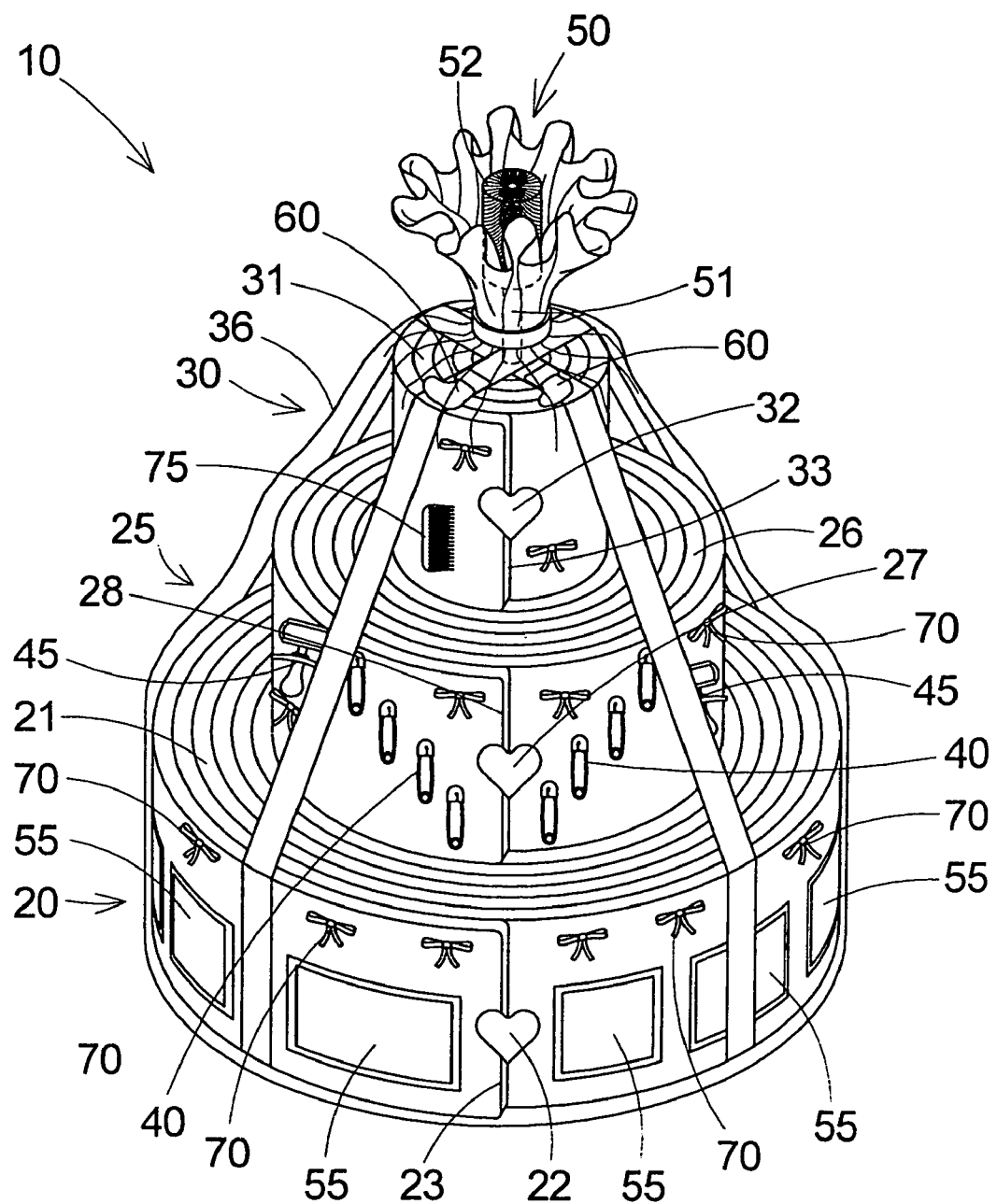
FIG. 1 is a schematic perspective view of a new infant accessory system and method of making the same according to the present invention.
Figure 2:
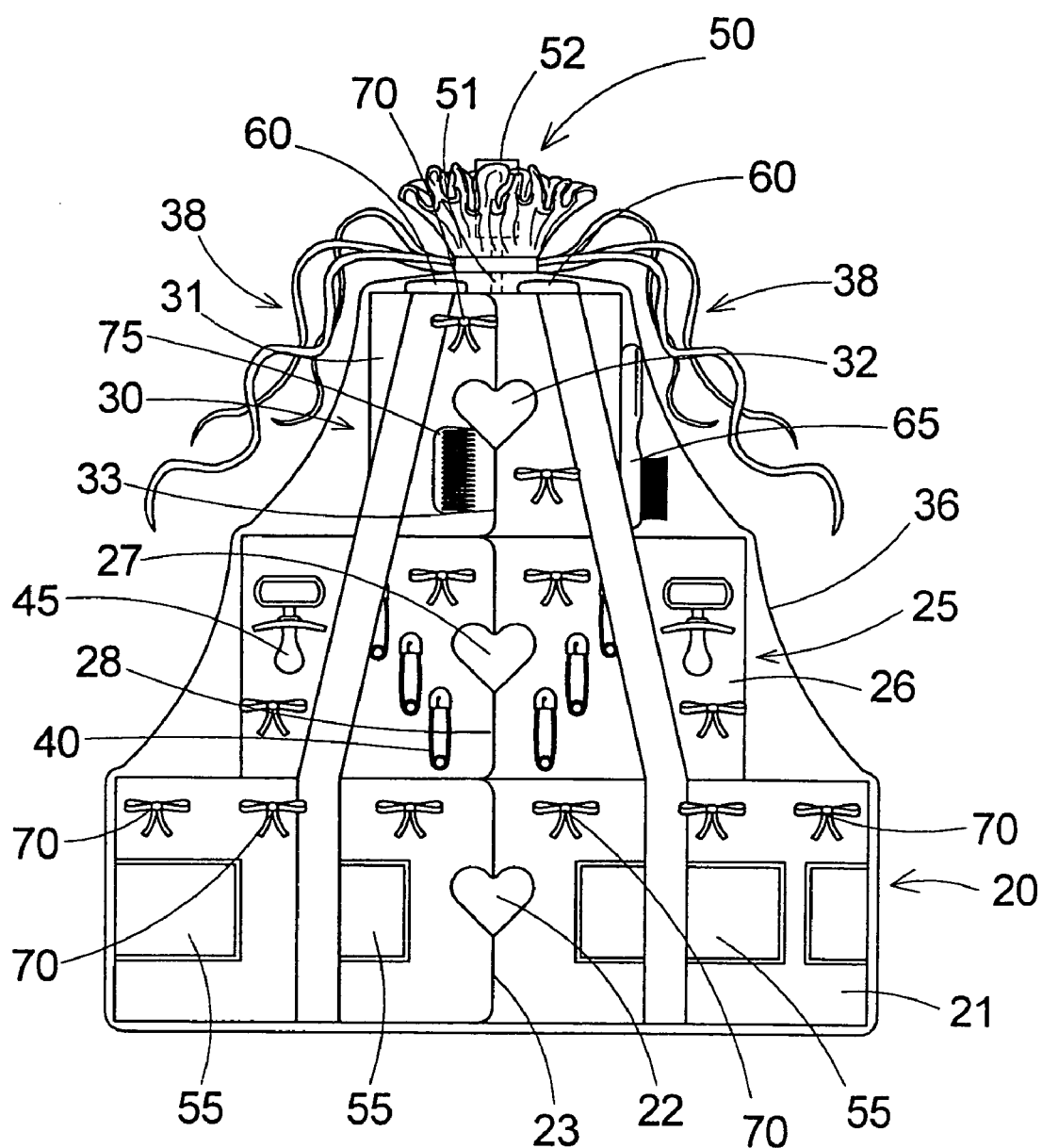
FIG. 2 is a schematic front view of the present invention.

With reference now to the drawings, and in particular to FIGS. 1 and 2 thereof, a new infant accessory system and method of making the same embodying the principles and concepts of the present invention and generally designated by the reference numeral 10 will be described.

As best illustrated in FIGS. 1 and 2, the infant accessory system and method of making the same 10 generally comprises a base layer 20, an intermediate layer 25, and a top layer 30.

The base layer 20 includes a plurality of diapers 21 rolled to form a cylindrical base. The base layer 20 includes a first diameter.

The intermediate layer 25 includes a second diameter less than the first diameter. The intermediate layer 25 includes a second plurality of diapers 26 rolled to form a cylindrical intermediate stage. The intermediate layer 25 is positioned on top of the base layer 20.

The top layer 30 includes a third diameter less than the second diameter. The top layer 30 includes a third plurality of diapers 31 rolled to form a cylindrical top layer. The top layer 30 is positioned on top of the intermediate layer 25.

Preferably, the base layer 20 further includes a securing means 22 for selectively securing an end of a last diaper 23 to an outer surface of the plurality of rolled diapers 21 to inhibit the plurality of diapers 21 from unrolling. Illustrative examples of a securing means 22 include tape, stickers, straight pins, or other suitable item.

Similarly, the intermediate layer 25 preferably further includes an intermediate securing means 27 for selectively securing an end of an intermediate last diaper 28 to an outer surface of the second plurality of rolled diapers 26 to inhibit the second plurality of diapers 26 from unrolling.

Likewise, the top layer 30 also preferably further includes a top securing means 32 for selectively securing an end of a top last diaper 33 to an outer surface of the third plurality of rolled diapers 31 to inhibit the third plurality of diapers 31 from unrolling.

A plurality of safety pins 40 an a plastic children's key ring may be operationally coupled to a selected layer of the system 10. Each one of the plurality of safety pins 40 is for selectively coupling an associated one of the plurality of diapers 21,26,31 to an infant.

At least one pacifier 45 and teething ring may be operationally coupled to a selected layer of the system 10. The pacifier 45 is for calming an infant.

Preferably, a baby bottle brush 50 having a handle portion 51 and a bristle portion 52, is positioned along a longitudinal axis of the top layer 30, with the bristle portion 52 abutting a top surface of the top layer 30.

A plurality of monetary items 55 may be operationally coupled to a selected layer of the system 10. Illustrative examples of monetary items 55 include cash, coupons, gift certificates, or any other suitable item.

A plurality of baby socks 60 may be positioned on a top surface of the top layer 30 of the system.

Preferably at least one baby brush 65 and baby rattle is operationally coupled to a selected layer of the system 10.

A wrapping member 36 may be used for selectively securing each of the base 20, intermediate 25, and top layers 30. Preferably, the wrapping member 36 is transparent, and may be tinted.

A plurality of ribbons 38 is used for selectively securing the wrapping member 36 around the base 20, intermediate 25, and top layers 30.

Each one of a plurality of bows 70 may be operationally coupled to an associated one of the base layer 20, intermediate layer 25, and the top layer 30.

Preferably, at least one baby comb 75 may be operationally coupled to a selected layer of the system 10.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An infant accessory system comprising:
   a base layer including a plurality of diapers rolled to form a cylindrical base, said base layer having a first diameter;
   an intermediate layer having a second diameter less than said first diameter, said intermediate layer including a second plurality of diapers rolled to form a cylindrical intermediate stage, said intermediate layer being positioned on top of said base layer;
   a top layer having a third diameter less than said second diameter, said top layer including a third plurality of diapers rolled to form a cylindrical top, said top layer being positioned on top of said intermediate layer; and
   a wrapping member for selectively securing each of said base, intermediate, and top layers, said wrapping member being transparent.

2. The system of claim 1, wherein said base layer further includes a securing means for selectively securing an end of a last diaper to an outer surface of said plurality of rolled diapers to inhibit said plurality of diapers form unrolling.

3. The system of claim 1, wherein said intermediate layer further includes an intermediate securing means for selectively securing an end of an intermediate last diaper to an outer surface of said second plurality of rolled diapers to inhibit said second plurality of diapers form unrolling.

4. The system of claim 1, wherein said top layer further includes a top securing means for selectively securing an end of a top last diaper to an outer surface of said third plurality of rolled diapers to inhibit said third plurality of diapers form unrolling.

5. The system of claim 1, further comprising a plurality of safety pins operationally coupled to a selected layer of said system, each one of said plurality of safety pins being for selectively coupling an associated one of said plurality of diapers to an infant.

6. The system of claim 1, further comprising at least one pacifier operationally coupled to a selected layer of said system, said pacifier being for calming an infant.

7. The system of claim 1, further comprising a baby bottle brush having a handle portion and a bristle portion, said handle portion being positioned along a longitudinal axis of said top layer, said bristle portion abutting a top surface of said top layer.

8. The system of claim 1, further comprising a plurality of monetary items operationally coupled to a selected layer of said system.

9. The system of claim 1, further comprising a plurality of baby socks positioned on a top surface of said top layer of said system.

10. The system of claim 1, further comprising at least one baby brush operationally coupled to a selected layer of said system.

11. The system of claim 1, further comprising a plurality of ribbons for selectively securing said wrapping member around said base intermediate and top layers.

12. The system of claim 1, further comprising a plurality of bows, each one of said plurality of bows being operationally coupled to an associated one of said base layer, intermediate layer, and said top layer.

13. The system of claim 1, further comprising at least one baby comb operationally coupled to a selected layer of said system.

14. An infant accessory system comprising:
   a base layer including a plurality of diapers rolled to form a cylindrical base, said base layer having a first diameter;
   an intermediate layer having a second diameter less than said first diameter, said intermediate layer including a second plurality of diapers rolled to form a cylindrical intermediate stage, said intermediate layer being positioned on top of said base layer;
   a top layer having a third diameter less than said second diameter, said top layer including a third plurality of diapers rolled to form a cylindrical top, said top layer being positioned on top of said intermediate layer;
   base layer further includes a securing means for selectively securing an end of a last diaper to an outer surface of said plurality of rolled diapers to inhibit said plurality of diapers form unrolling;
   said intermediate layer further includes an intermediate securing means for selectively securing an end of an intermediate last diaper to an outer surface of said second plurality of rolled diapers to inhibit said second plurality of diapers form unrolling;
   said top layer further includes a top securing means for selectively securing an end of a top last diaper to an outer surface of said third plurality of rolled diapers to inhibit said third plurality of diapers form unrolling;
   a plurality of safety pins operationally coupled to a selected layer of said system, each one of said plurality of safety pins being for selectively coupling an associated one of said plurality of diapers to an infant;
   at least one pacifier operationally coupled to a selected layer of said system, said pacifier being for calming an infant;
   a baby bottle brush having a handle portion and a bristle portion, said handle portion being positioned along a longitudinal axis of said top layer, said bristle portion abutting a top surface of said top layer;
   a plurality of monetary items operationally coupled to a selected layer of said system;
   a plurality of baby socks positioned on a top surface of said top layer of said system;
   at least one baby brush operationally coupled to a selected layer of said system;

a wrapping member for selectively securing each of said base, intermediate, and top layers, said wrapping member being transparent;

a plurality of ribbons for selectively securing said wrapping member around said base intermediate and top layers;

a plurality of bows, each one of said plurality of bows being operationally coupled to an associated one of said base layer, intermediate layer, and said top layer; and at least one baby comb operationally coupled to a selected layer of said system.

15. A method of making an infant accessory system comprising:

providing a plurality of diapers;

rolling said plurality of diapers to form a cylindrical base, said base layer having a first diameter;

providing a second plurality of diapers;

rolling said second plurality of diapers to form an cylindrical intermediate layer having a second diameter less than said first diameter form a cylindrical intermediate stage;

positioning said intermediate layer on top of said base layer;

providing a third plurality of diapers;

rolling said third plurality of diapers to form a cylindrical a top layer having a third diameter less than said second diameter;

positioning said top layer on top of said intermediate layer;

providing a securing means for selectively securing an end of a last diaper to an outer surface of said plurality of rolled diapers to inhibit said plurality of diapers form unrolling;

providing an intermediate securing means for selectively securing an end of an intermediate last diaper to an outer surface of said second plurality of rolled diapers to inhibit said second plurality of diapers form unrolling;

providing a top securing means for selectively securing an end of a top last diaper to an outer surface of said third plurality of rolled diapers to inhibit said third plurality of diapers form unrolling;

providing a plurality of safety pins;

coupling operationally each one of said plurality of safety pins to a selected layer of said system, each one of said plurality of safety pins being for selectively coupling an associated one of said plurality of diapers to an infant;

providing at least one pacifier;

coupling operationally said at least one pacifier to a selected layer of said system, said pacifier being for calming an infant;

providing a baby bottle brush having a handle portion and a bristle portion;

positioning said handle portion along a longitudinal axis of said top layer, said bristle portion abutting a top surface of said top layer;

providing a plurality of monetary items;

coupling operationally each one of said plurality of monetary items to a selected layer of said system;

providing a plurality of baby socks;

positioning each one of said pair of baby sock on a top surface of said top layer of said system;

providing at least one baby brush;

coupling operationally said at least one baby brush to a selected layer of said system;

providing a plurality of bows;

operationally coupling each one of said plurality of bows to an associated one of said base layer, intermediate layer, and said top layer;

providing at least one baby comb;

coupling operationally said at least one baby comb to a selected layer of said system;

providing a wrapping member for selectively securing each of said base, intermediate, and top layers, said wrapping member being transparent;

providing a plurality of ribbons for selectively securing said wrapping member around said base intermediate and top layers wrapping said wrapping member around each of said base, intermediate, and top layers; and securing said wrapping member with said plurality of ribbons.

* * * * *